US011602478B2

(12) United States Patent
Prattichizzo et al.

(10) Patent No.: US 11,602,478 B2
(45) Date of Patent: Mar. 14, 2023

(54) HAPTIC SYSTEM FOR PROVIDING A GAIT CADENCE TO A SUBJECT

(71) Applicant: UNIVERSITA' DEGLI STUDI DI SIENA, Siena (IT)

(72) Inventors: Domenico Prattichizzo, Siena (IT); Simone Rossi, Siena (IT); David Cioncoloni, Monteriggioni (IT); Tommaso Lisini Baldi, Siena (IT); Mostafa Mohammadi, Berlin (DE); Marco Aggravi, Sarteano (IT)

(73) Assignee: UNIVERSITA' DEGLI STUDI DI SIENA, Siena (IT)

( * ) Notice: Subject to any disclaimer, the term of this patent is extended or adjusted under 35 U.S.C. 154(b) by 422 days.

(21) Appl. No.: 16/099,516

(22) PCT Filed: May 16, 2017

(86) PCT No.: PCT/IB2017/052887
§ 371 (c)(1),
(2) Date: Nov. 7, 2018

(87) PCT Pub. No.: WO2017/199171
PCT Pub. Date: Nov. 23, 2017

(65) Prior Publication Data
US 2019/0105217 A1    Apr. 11, 2019

(30) Foreign Application Priority Data
May 16, 2016    (IT) .................... 102016000050153

(51) Int. Cl.
*A61H 3/00*    (2006.01)
*A61B 5/00*    (2006.01)
(Continued)

(52) U.S. Cl.
CPC .............. *A61H 3/00* (2013.01); *A61B 5/1038* (2013.01); *A61B 5/112* (2013.01); *A61B 5/4836* (2013.01);
(Continued)

(58) Field of Classification Search
CPC .............. A61H 3/00; A61H 2201/5015; A61H 2201/5012; A61H 2201/5035;
(Continued)

(56) References Cited

U.S. PATENT DOCUMENTS 7,785,279 B2 * 8/2010 Sankai .................. A61F 5/0102
601/5
8,972,017 B2 * 3/2015 Dar ....................... A61B 5/6807
607/48
(Continued)

FOREIGN PATENT DOCUMENTS

DE    10 2011 076 891 A1    12/2012
WO    2015/088863 A2    6/2015

OTHER PUBLICATIONS

International Search Report, dated Oct. 5, 2017, corresponding to Application No. PCT/IB2017/052887.

*Primary Examiner* — Timothy A Stanis
*Assistant Examiner* — Kelsey E Baller
(74) *Attorney, Agent, or Firm* — Ladas & Parry LLP; Malcolm J. MacDonald

(57) ABSTRACT

A haptic system for providing a gait cadence to a subject comprising a portable telecommunication device with a control unit and a wireless transmission means; a vibrotactile device configured to be tightly worn on a portion of the subject's body, including at least one motor configured to generate vibrations that can be perceived by the subject and an actuation unit configured to actuate the motor. The actuation unit is configured to receive wireless signals from
(Continued)

the wireless transmission means of the portable telecommunication device and to cause the motor to produce vibrations responsive to the wireless signals. In the control unit a generation program is resident configured to generate cadence signals and to transmit the wireless signals responsive to the cadence signals by the wireless transmission means to the actuation unit. The generation program is configured to provide corresponding cadence pulses to the motor.

9 Claims, 13 Drawing Sheets

(51) Int. Cl.
A61H 39/00 (2006.01)
A61B 5/11 (2006.01)
A61B 5/103 (2006.01)
A61H 23/02 (2006.01)

(52) U.S. Cl.
CPC ........... *A61B 5/6828* (2013.01); *A61H 23/02* (2013.01); *A61H 39/007* (2013.01); *A61B 2505/09* (2013.01); *A61B 2562/0219* (2013.01); *A61B 2562/04* (2013.01); *A61H 2003/007* (2013.01); *A61H 2201/165* (2013.01); *A61H 2201/5012* (2013.01); *A61H 2201/5015* (2013.01); *A61H 2201/5035* (2013.01); *A61H 2201/5084* (2013.01); *A61H 2201/5097* (2013.01)

(58) Field of Classification Search
CPC .......... A61H 2201/5084; A61B 5/1114; A61B 5/1115; A61B 5/1116; A61B 5/1117; A61B 5/112; A61B 5/1121; A61B 5/1122; A61B 5/1123; A61B 5/6828; A61B 5/4836; A63B 71/0686; G01C 22/006
See application file for complete search history.

(56) References Cited

U.S. PATENT DOCUMENTS

| | | | |
|---|---|---|---|
| 9,526,946 B1* | 12/2016 | Zets | A61B 5/6892 |
| 9,558,399 B1* | 1/2017 | Jeka | G06K 9/00523 |
| 2006/0129308 A1 | 6/2006 | Kates | |
| 2007/0173903 A1 | 7/2007 | Goren et al. | |
| 2007/0203435 A1 | 8/2007 | Novak | |
| 2007/0299374 A1* | 12/2007 | Gesotti | A61H 23/02 |
| | | | 601/79 |
| 2008/0139975 A1 | 6/2008 | Einav et al. | |
| 2011/0153197 A1* | 6/2011 | Song | A61B 5/1112 |
| | | | 701/533 |
| 2012/0154153 A1* | 6/2012 | Agrawal | A61B 5/0051 |
| | | | 340/573.1 |
| 2012/0259255 A1 | 10/2012 | Tomlinson et al. | |
| 2013/0218456 A1 | 8/2013 | Zelek et al. | |
| 2015/0297934 A1* | 10/2015 | Agrawal | A61H 1/0266 |
| | | | 482/4 |
| 2017/0065849 A1* | 3/2017 | Konishi | A61B 5/112 |
| 2017/0119553 A1 | 5/2017 | Cipriani et al. | |
| 2018/0289287 A1* | 10/2018 | Sio | A61B 5/486 |
| 2019/0120733 A1* | 4/2019 | Jiang | G01N 11/04 |
| 2020/0306567 A1* | 10/2020 | Wallace | G08B 25/016 |

* cited by examiner

HAPTIC SYSTEM FOR PROVIDING A GAIT CADENCE TO A SUBJECT

FIELD OF THE INVENTION

The present invention relates to a system to drive a subject to walk or to jump or to run maintaining a predetermined gait cadence.

PRIOR ART

The need of driving one or more people to walk maintaining a given gait cadence is felt in several fields.

In particular, this it is necessary in order to rehabilitate patients who walk asymmetrical and/or irregularly, typically due to a cerebrovascular hit or to some nervous system disease such as Parkinson's disease or from peripheral neuropathy. Such an irregular gait can cause the patient to fall down, to hit against objects and, with the time, it can be the origin of painful muscle and bone illnesses.

Medical sensory substitution devices are known that aim at restoring a patient's sensitivity and awareness of his/her own gait, which has been compromised by a peripheral neuropathy. This awareness is necessary for the patient to walk correctly. In particular, WO 2012/142041 A1 and US 2007/0173903 A1 propose systems comprising sensors, such as accelerometers, to provide a feedback about an ongoing gait, a means for collecting, processing and sending related signals to a haptic device of the system arranged at a patient's sensory sound region, and configured to change these signals into vibrotactile stimulations, by which the patient becomes aware again of his/her own gait progression and can recognize, in particular, the initial contact and the toe-off stages carried out by each foot.

WO 2005/086574 A2 describes a rehabilitation device in which a sensorized support element for a patient's limb, along with possible position sensors and/or accelerometers, can follow the limb movements and produce related position signals, a music generator and a control device for receiving the signals and modifying the rhythm of the music emitted by the generator according to the movements.

WO 2015/088863 A2 describes a rehabilitation garment for of a patient in an exemplary embodiment of which piezoelements are provided that are configured to producing subliminal vibrations.

The need of providing a gait cadence to one or more subjects can occur also when a performance improvement is sought for one or more athletes, in order to achieve a target performance or a performance that a trainer shows, by his own gait cadence, during a training session. However, such a need can also occur in a rehabilitation procedure. At any rate, in some instances some people can desire synchronizing their own gait cadences while moving along respective paths that are far away from one another, just for amusement.

Providing a gait cadence, and possibly synchronising the gait cadence of a few people can also be required in a method of guiding one or more subjects along one or more predetermined paths, in particular, in order to cover the path in a predetermined time and/or in order to reach a predetermined meeting place, without exchanging messages that can be intercepted by a third party, such as radio messages and the like.

Guiding systems are known, in particular for partially sighting or blind people, for instance, from US2006129308A1 and by PI2014A000016, the latter in the name of the same applicants of the present application. GPS-assisted haptic systems providing direction data are also known from US2013218456.

SUMMARY OF THE INVENTION

It is therefore a feature of the invention to provide a rehabilitation system for providing a gait cadence to a patient who walks asymmetrically and/or irregularly due to a cerebrovascular hit or to some nervous system disease such as Parkinson's disease, which allows to restore a regular gait cadence in a shorter time and with lower stress and discomfort for the patient.

It is another feature of the invention to provide a system for synchronizing the gait cadence of a few people, in particular, to the gait cadence shown by a sport or rehabilitation trainer or for allowing gait cadence synchronization to a few people running or walking along paths that are far away from one another.

It is also a feature of the invention to provide a system for guiding one or more subjects along a path that is at least in part unknown to the subject(s), so as to move from a respective starting position to a respective destination, in particular to a common meeting position, in particular, in a predetermined time, and without exchanging messages that can be intercepted by a third party.

These and other objects are achieved by a haptic system for providing a gait cadence to a subject, the system comprising:
  a portable telecommunication device comprising a control unit and a wireless transmission means;
  a vibrotactile device configured to be tightly worn on a portion of the subject's body, and comprising:
    at least one motor configured to generate vibrations that can be perceived by the subject;
    an actuation unit configured to actuate the motor,
  wherein
  the actuation unit is configured to receive wireless signals from the wireless transmission means of the portable telecommunication device and to cause the motor to produce vibrations responsive to the wireless control signals;
  in the control unit a generation program is resident configured to generate cadence signals and to transmit the wireless signals responsive to the cadence signals by the wireless transmission means of the portable telecommunication device to the actuation unit;
  the generation program is configured to cause the motor to generate corresponding cadence pulses, in order to cause said motor to generate said vibrations, in such a way that the subject can cadence his/her own gait responsive to the pulses, the program configured to generate, through the cadence signals:
    a cadence pulse rate set between 0.5 and 3 pulses per second;
    a single pulse duration set between 0.1 and 1.0 second;
    a repetition of the pulses for at least 30 seconds.

This way, a subject who wears the haptic system can adjust the gait cadence, when walking or running, to such vibration pulses.

In particular, for patients suffering from Parkinson's disease, has been verified that a predetermined gait cadence, which a doctor can assess as suitable for each single patient, can assist the patient to walk properly, thus obtaining beneficial health effects for the patient. Actually, a parkinsonian subject cannot easily maintain a prefixed gait cadence, and the vibratory haptic stimulation assists the muscular actuation decision process that is required to begin a step.

Preferably, the haptic system comprises a couple of right and left vibrotactile devices, each having:
respective right and left motors, each configured to generate vibrations that can be perceived by the subject;
respective right and left actuation units, configured to actuate the right motor and the left motor, respectively;
and each configured to be tightly worn on a right part and on a left part of said subject's body, with respect to the middle sagittal plane of the body, and wherein the generation program is configured to cause the right motor and the left motor to alternatively generate the cadence pulses, globally respecting the cadence pulse rate, which is set between 0.5 and 3 pulses per second.

This way, the subject perceives vibrotactile pulses on the right part and on the left part of his/her own body, at an alternated rate, which assists maintaining the predetermined gait cadence. This is particularly advantageous for those patients, such as people suffering from Parkinson's disease, who have asymmetric posture and motion of his/her right and left body parts. Actually, by providing regularly alternate cadenced pulses both on the right part and on the left part, typically on the right limb and on the left limb, the patient can be rehabilitated to move his/her right and left limbs according to a regular gait cadence, and to assume a symmetrical body posture.

In an exemplary embodiment, the system comprises a sensor configured to provide position signals of a lower limb in a gait cycle to the control unit, and the generation program resident in the control unit is configured to modify the cadence pulse rate responsive to such position signals.

This way, the subject can wear the sensor and receive the vibrotactile stimulations when a determined step of the gait cycle takes place, for instance whenever the foot touches the soil and whenever the foot all the times that occurs the abutment of the foot to ground, or whenever the foot is detached from the soil. This is the case, in particular, of an exemplary embodiment of the system in which the sensor is integral to the vibrotactile device. This configuration is advantageous because, as shown by experimental tests, the gait synchronization to a regular cadence, i.e. providing a gait cadence, is obtained more quickly if the stimulations are not given regardless to the subject's initial gait, but they are given at a predetermined step of the gait cycle, for example at the initial contact step or at the toe-off step.

In another point of view, in some exemplary embodiments, systems comprising position sensors for providing lower limbs position signals during the gait cycle, can obtain a feedback on the actual subject's gait conditions and, through such a system, this feedback can be notified to a possible remote operator or assistant.

In a particular exemplary embodiment, or in a particular operation mode, the system can also adjust the gait cadence required to the subject according to a performance the subject can achieve. In other words, if the subject has a gait cadence that is always higher than the value calculated by the control unit, the latter adjusts the required gait cadence to a value that is at least the same as the one detected by the position signals or the same as an average value calculated with reference to a predetermined number of recent steps. On the contrary, if the subject has a gait cadence that is always lower than the value calculated by the control unit, the latter adjusts the required gait cadence to a value that is at most equal to or slightly higher than what detected through the position signals, or the same as said average value.

In particular, the control unit is configured to measure a current step rate according to the position signals and to compare the current step rate with a current value of the cadence pulse rate, and the generation program resident in the control unit is configured to modify the cadence pulse rate from the current value to a modified value corresponding to the current step rate, if the current step rate is not modified within a predetermined time. In particular, this change of the current step rate is provided if the current step rate is not modified within a time maximum set between 5 and 10 seconds.

This way, the subject who moves at a gait rate corresponding to the current cadence pulse rate can modify the cadence pulse rate by increasing or decreasing the gait cadence for a time equal to or longer than the predetermined time. This allows the subject to change the cadence pulse rate without stopping or without changing the settings of the portable telecommunication device while advancing. Moreover, the predetermined time is selected in such a way that a possible temporary step rate decrease or a stop are not understood by the system as if the subject wished to change the step rate.

In particular, the sensor comprises a pressure or contact sensor, and the position signals are pressure signals or signals responsive to the contact between a foot of the lower limb and the soil. This makes it possible to integrate the sensor in an insole of a shoe with which the subject can be provided, or which can be a part of the system. In particular, this makes it possible to integrate a plurality of sensors at different positions of the insole, in order to describe and notify to the control unit particular positions of the foot as long as the latter is in contact with the soil, responsive to the amount and to the position of the sensors that are in a contact or compression condition, due to the instantaneous contact of the insole with the soil. This allows providing the vibrotactile stimulations at a precise step of the gait cycle.

As an alternative, or in addition, the sensor comprises an accelerometer, and the position signals are accelerometer signals. This makes it possible to describe and notify to the control unit particular positions of the foot even when the latter is no longer in contact with the soil, which allows providing vibrotactile stimulations even when the foot is not in contact with the soil.

In an exemplary embodiment, the sensor is separate from the vibrotactile device. This way, the sensor, regardless it is an accelerometer or a pressure or contact sensor, can be worn by someone who is not the same person as the subject, and who performs an exemplary gait at the same time as the subject. This person and the subject can be a rehabilitation trainer and a patient suffering from a nervous system diseases such as the Parkinson's disease, or from peripheral neuropathy, respectively, or they can be a sport trainer and a subject or sportsman who wants to achieve a regular gait while running or walking, or to improve his/her own performances. The device according to this exemplary embodiment allows an emulation process by the subject through a sensory-motor channel. Actually, a stimulation provided through such channel makes it possible to obtain a synchronisation to a desired gait cadence more effectively and more quickly than a stimulation made through visual or acoustic communications channels only.

In a system according to an advantageous exemplary embodiment of the invention, comprising a sensor configured to provide position signals of a lower limb in a gait cycle, the portable telecommunication device is a first portable telecommunication device with a first control unit and a first wireless transmission means, and the vibrotactile device is a first vibrotactile device with a first motor and a first actuation unit, and the system also comprises:
- a second portable telecommunication device comprising a second control unit and second wireless transmission means;
- a second vibrotactile device comprising a second motor configured to generate vibrations that can be perceived by a second subject and comprising a second actuation unit configured to actuate the second motor;

the second actuation unit configured to receive wireless signals from the second wireless transmission means of the second portable telecommunication device and to cause vibrations of the second motor responsive to the wireless signals, wherein the first control unit is configured to measure a first current step rate starting from the position signals provided by the sensor, and for wirelessly communicating the first current step rate to the second portable telecommunication device, wherein in the second control unit a cadence signals generation program is resident configured to generate cadence signals and to transmit the cadence signals through the second wireless transmission means to the second actuation unit, wherein the second actuation unit is configured to receive wireless signals from the second wireless transmission means and to cause vibrations of the second motor responsive to the wireless signals, This way, a first subject or a master subject, or a main subject, who wears the first couple of vibrotactile devices, can haptically communicate his/her own step rate to a second subject or slave subject, or subordinate subject, who wears the second vibrotactile device, similarly to what is possible by the above-described embodiments comprising an accelerometer, or a contact/pressure sensor, or another kind of sensor for measuring the position of the limbs, separate from the vibrotactile device. In this case, however, due to the presence of two different portable telecommunication devices, it is possible to enable this haptic communication process and it is therefore possible to synchronise the two subjects' gait cadence, even if they are far away from each other by kilometers. By this exemplary embodiment, rehabilitation or training sessions can be organized for a patient and for a sportsman, respectively, by a remote rehabilitation/sport trainer, with respect to the person to whom the cadence pulses are addressed. More in general, social running or collective running sessions can be carried out by two or more than two subjects that are far away from one another, wherein one of the subjects plays the role of leader or master subject, and the other(s) aim(s) at synchronizing to the master subject.

In an exemplary embodiment, in the second vibrotactile device a second sensor is provided configured to provide position signals of a lower limb of the second subject in a gait cycle, and the second control unit is configured to measure a second current step rate of the second subject starting from position signals coming from the second sensor, and to notify the second current step rate to the first portable telecommunication device.

This way, the first subject and the second subject can mutually synchronize their own gait cadence by a haptic means. For instance, whenever one of the two subjects begins to modify his/her own step rate, he imposes this rate change to the other subject. In particular, this is useful to perform social or collective running events in which two or more than two subjects wishes to wherein two or more subject wish to run and mutually synchronize their own gait cadence.

In an exemplary embodiment, the system can comprise:
- a plurality of vibrotactile devices with respective motors and actuation devices;
- a plurality of portable telecommunication devices with respective control units and wireless communication means;
- a plurality of sensors configured to provide position signals of a lower limb of a respective subject who wears one of said vibrotactile devices in a gait cycle, and said generation program, which is resident in each control unit, is configured to cause a respective motor to generate cadence pulses having a rate equal to an average value of rate values detected starting from said position signals.

In an advantageous exemplary embodiment, portable telecommunication device 16 comprises a navigation system 43 configured to generate direction signals 66 according to a predetermined path selected for the subject, whereas the control unit 17 is configured to transmit to the actuation unit 14 further wireless signals 45 responsive to direction signals 66, so that the actuation unit 14 causes the motor 12 to generate direction pulses 49, where direction pulses 49 differ from cadence pulses 19 by at least one feature selected among the pulse duration, the repetition of the cadence pulses and an intensity of the cadence pulses.

In particular, in a system with right and left vibrotactile devices, the control unit 17 is configured to transmit the further wireless signals 45 responsive to right and left direction signals 66 to the right 14d,24d actuation unit and to the left actuation unit 14s,24s, respectively. This way, the actuation unit 14 causes the right motor 12d,22d and the left motor 12s,22s to generate right and left direction pulses 49, respectively. In particular, the control unit 17 is configured to transmit the further wireless signals responsive to stop or U-turn direction signals 66 to both right 14d,24d and left 14d,24d actuation unit. This way, the actuation unit 14 causes both right 12d,22d and left 12s,22s motors to generate stop or U-turn direction pulses 49.

In another advantageous exemplary alternative embodiment, as an alternative to the previous one, portable telecommunication device 16 similarly comprises the navigation system 43, and the control unit 17 is configured to as in the previous exemplary embodiment. Moreover, the vibrotactile device comprises a further motor 38 arranged at a predetermined distance from the motor 12,22, and the actuation unit 14,24 is configured to cause the further motor 38 to generate direction pulses 49, in such a way that the subject perceives the direction pulses and the cadence pulses at different points of his/her body part 6.

In particular, in a system with right and left vibrotactile devices having further right and left motors 38, respectively, configured to generate vibrations that can be perceived by the subject, the actuation unit 14,24 is configured to cause the further right and left motor 38 to generate right and left direction pulses 49, respectively, and to cause both right and left further motors 38 to generate stop and U-turn direction pulses 49.

In an exemplary embodiment, the motor comprises a driven rotating shaft including an eccentrical portion. Such motors are normally used in some portable telephone devices to obtain various signals in the form of vibrations, and are not expensive, which allows limiting the production costs of the system.

As an alternative, the motor can be a voice coil-type motor. This kind of motor makes it possible to control the vibration amplitude and frequency independently from each other, and allows therefore codifying different type of information by changing either of these physical quantities associated to the cadence pulses, for example, in order to distinguish the direction pulses from the cadence gait pulses in the case of a vibrotactile unit having a single motor.

BRIEF DESCRIPTION OF THE DRAWINGS

The invention will be now shown with the following description of its exemplary embodiments, exemplifying but not limitative, with reference to the attached drawings, in which.

DETAILED DESCRIPTION OF THE INVENTION

Figure 1:
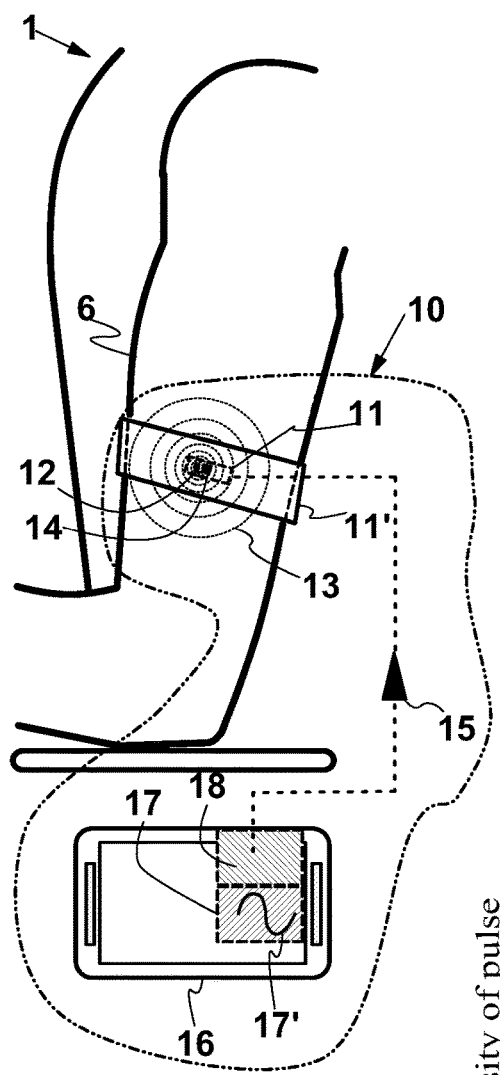
FIG. 1 shows a haptic system for providing a gait cadence to a subject according with a first exemplary embodiment of the invention.

With reference to FIG. 1, a haptic system 10 for providing a gait cadence to a subject 1, according to a first exemplary embodiment of the invention, comprises a vibrotactile device 11 configured to be tightly worn on a part of the body 6 of subject 1.

Figure 5:
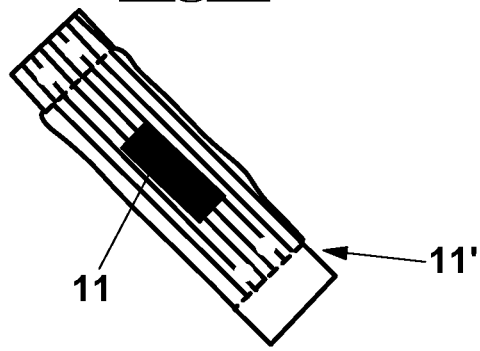
FIG. 5 shows a vibrotactile device arranged on a band to be worn by a subject.

As FIG. 5 also shows, vibrotactile haptic device 11 can be connected to a band 11', or can comprise band 11', for example the band 11' of a bracelet (FIG. 1), or of a garment to be worn on another part of the body.

Figure 10:
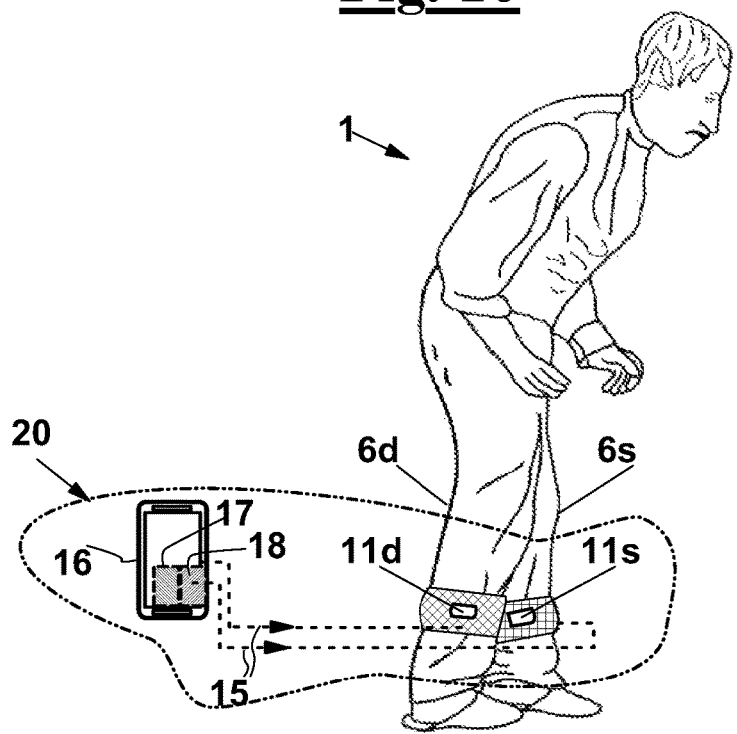
FIG. 10 shows a system according with another exemplary embodiment of the invention, in which a couple of right and left vibrotactile devices is provided.
Figure 16:
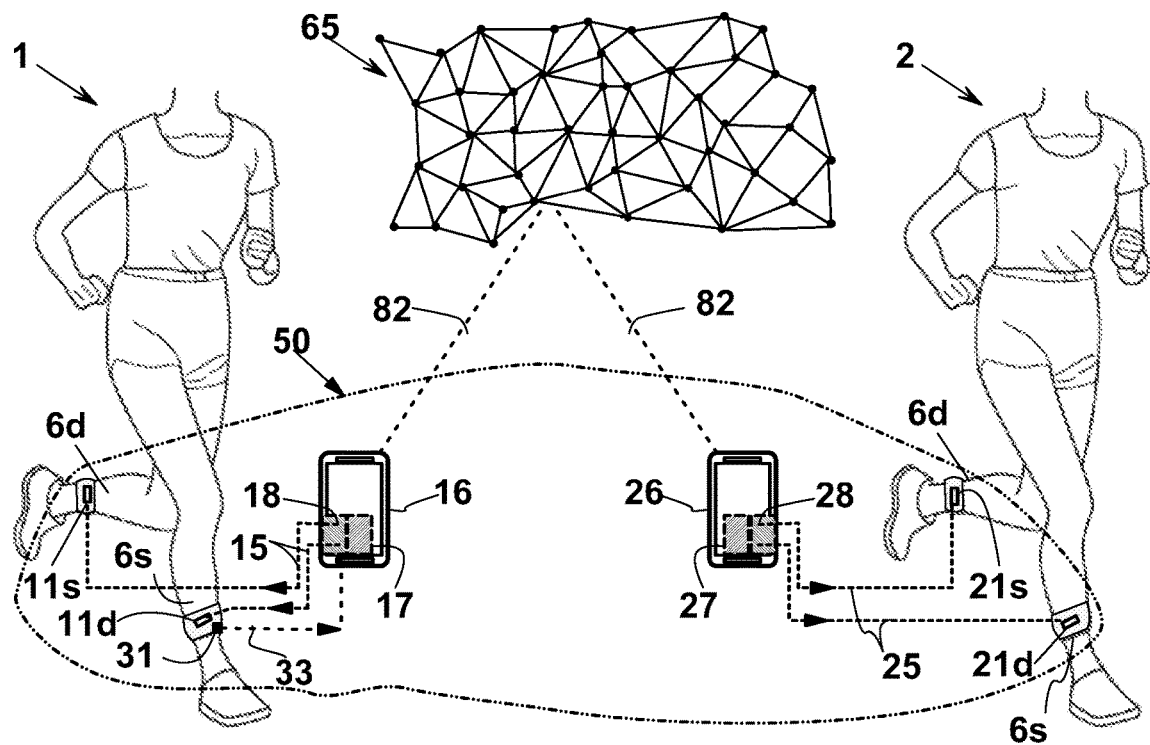
FIGS. 16 and 17 show systems second further exemplary embodiments of the invention, in which two vibrotactile devices or two couples of vibrotactile devices are provided for two different subjects, for a remote training or social running purpose.
Figure 17:
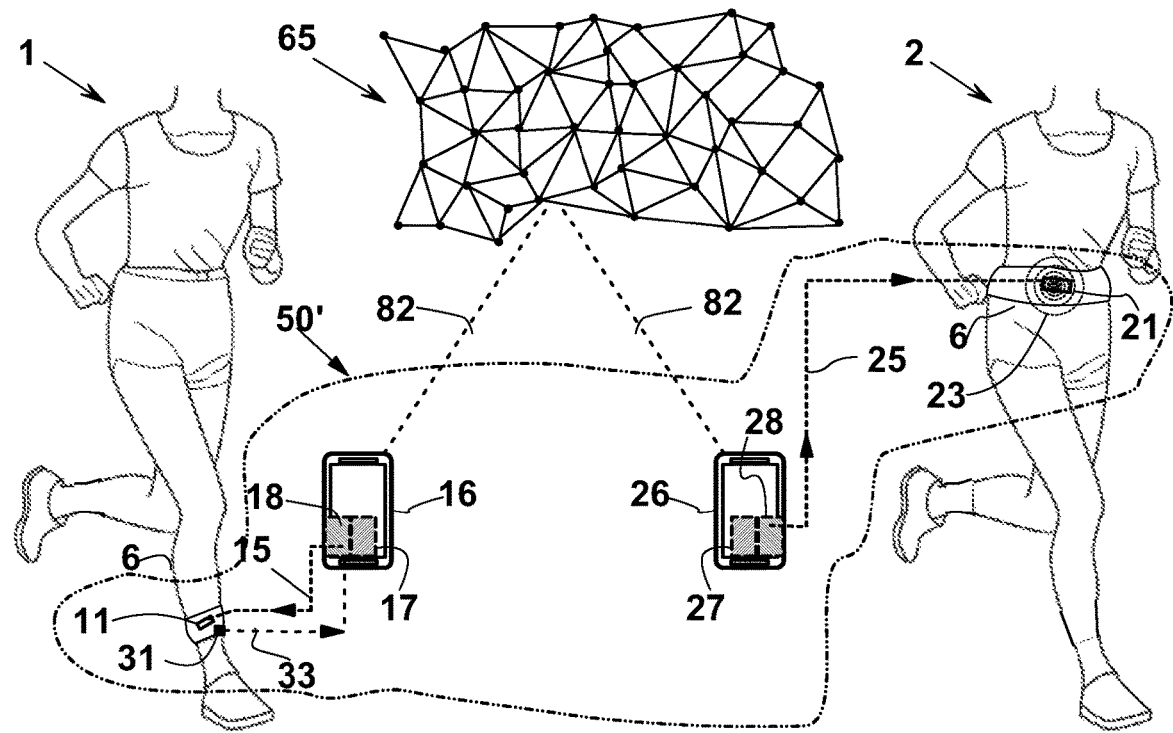
Figure 23:
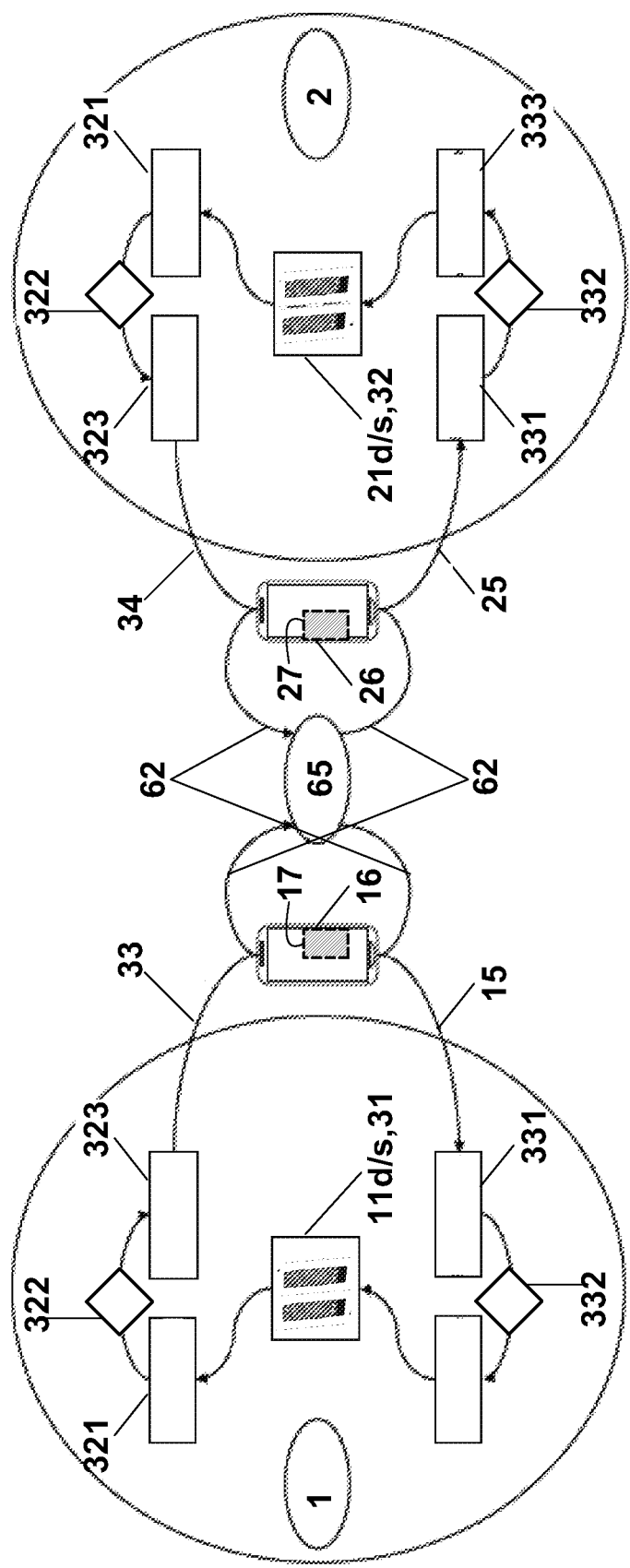
FIG. 23 shows a diagrammatical showing the elements of the system according to the modification of FIG. 18 along with the steps of the procedure shown in FIG. 22.
Figure 24:
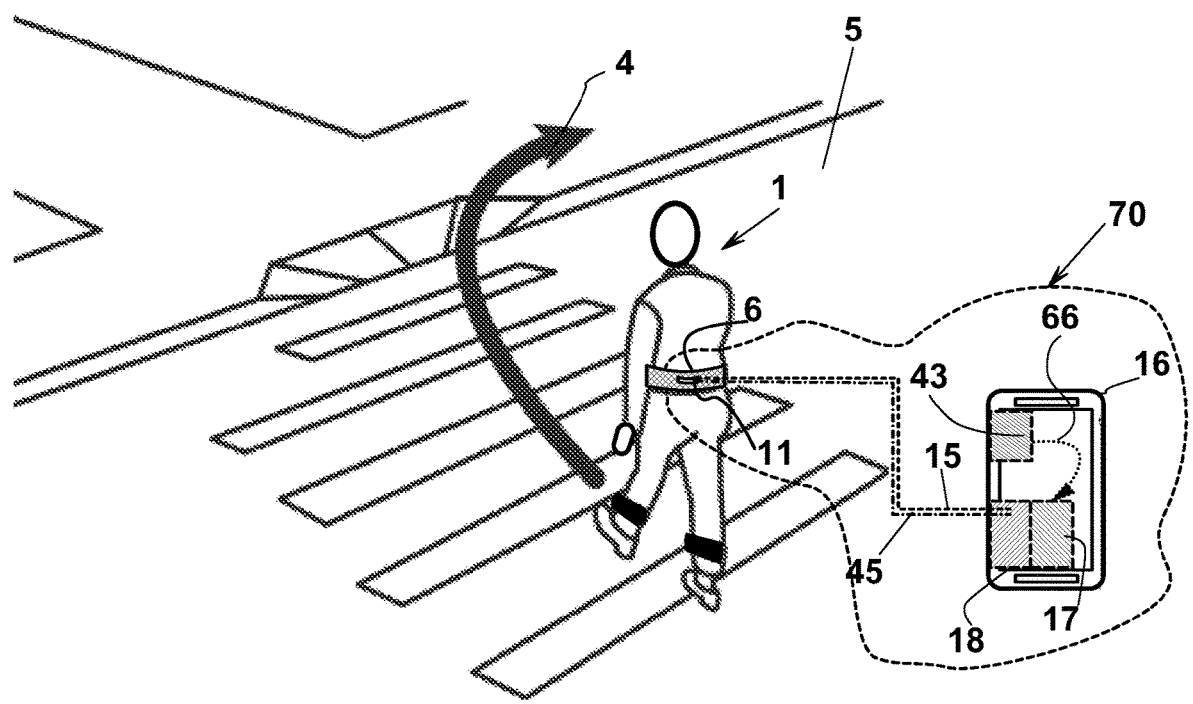
FIGS. 24 and 25 diagrammatically show a system according to further embodiments of the invention, configured to provide direction pulses to a subject, as well as gait pulses, comprising respectively one and two vibrotactile device(s) that can be worn on corresponding body parts of the subject.

The body part on which or about which vibrotactile haptic device 11 is configured to be worn, can be, for instance, an arm 6, as in FIG. 1, but also a forearm, or a leg 6,6d,6s, as shown, for example, in FIGS. 10, 17 and 23, or can be a body part different from a limb, such as the waist 6 of FIGS. 16 and 24.

As also shown in FIG. 1, haptic system 10 comprises, besides vibrotactile device 11, a portable telecommunication device 16, in which wireless transmission means 18 is prearranged, as well as a control unit 17, configured to transmit wireless signals 15 through wireless transmission means 18.

More in detail, a program means is resident in control unit 17 of portable telecommunication device 16 to generate wireless signals 15 and to transmit the latter to actuation unit 14 of vibrotactile device 11, by wireless transmission means 18.

Figure 6:
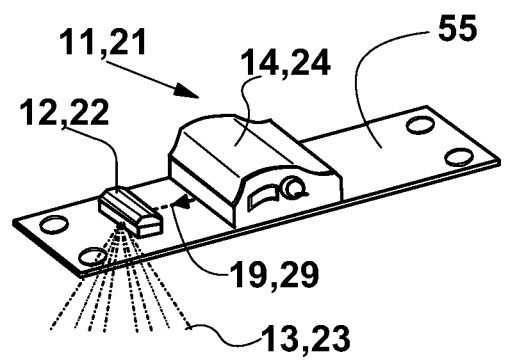
FIG. 6 diagrammatically shows the structure of a vibrotactile haptic device comprising a single motor.

As shown in FIGS. 1 and 6, vibrotactile device 11 comprises at least one motor 12 configured to generate vibrations 13 (FIG. 1) that can be perceived by subject 1 at his/her own body part 6, and an actuation unit 14 configured to operate motor 12.

More in detail, actuation unit 14 is configured to receive wireless signals 15 and to produce drive electrical signals, not shown, responsive to wireless signals 15, whereas motor 12, which is in electrical communication with actuation unit 14 so as to receive the drive electrical signals, is configured to generate said vibrations, i.e. cadence pulses 19. The program means of control unit 17 is then configured to cause motor 12 to generate cadence pulses 19 in the form of vibrations, responsive to wireless signals 15.

In the exemplary embodiment as shown, motor 12 and actuation unit 14 are mounted on a same support 55, typically on a flexible support, or on a flexible printed circuit, which can be embedded in band 11' and arranged on body part 6 of subject 1 along with it.

Figure 2:
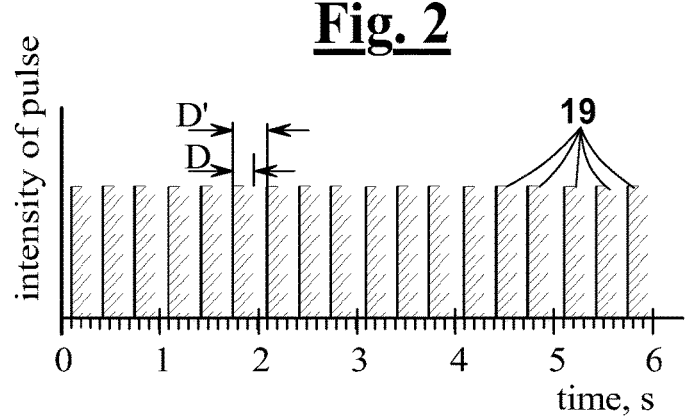
FIGS. 2 and 3 diagrammatically show the cadence pulse rate and the single pulse duration of cadence pulses generated by the vibrotactile devices of the system according to the invention.
Figure 3:
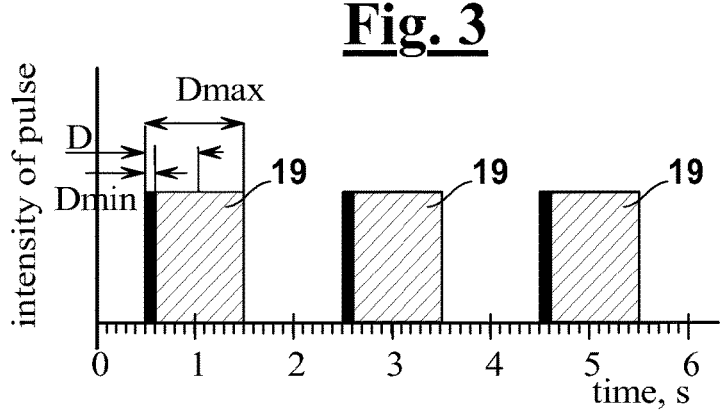

According to the invention, each cadence pulse 19 has a length D set between a minimum value $D_{min}$ of 0.1 s and a maximum value $D_{max}$ of 1 s, as shown in FIG. 3. The cadence pulse rate is set between 0.5 pulses per second, as in FIG. 3, and 3 pulses per second, as in FIG. 2.

Figure 4:
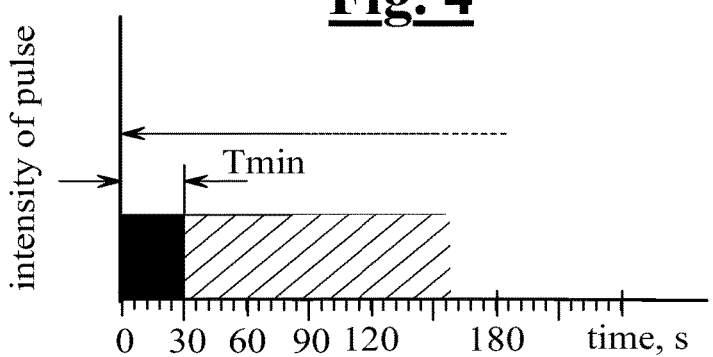
FIG. 4 diagrammatically shows the duration of a sequence or repetition of said cadence pulses.

As shown in FIG. 4, the minimum duration T of a repetition or train or sequence of pulses is longer than a minimum value Tmin of 30 seconds.

Vibrating motor 12 is preferably configured to be controlled by control unit 17, for example, by the Blueetooth communication protocol, i.e. through Blueetooth signals 15.

In an exemplary embodiment, motor 12 comprises a driven rotating shaft having an eccentrical portion. This type of motors is normally used in the portable telephone devices, and makes it possible to easily generate vibrations that can be perceived by a subject with a minimum energy consumption.

Figure 7:
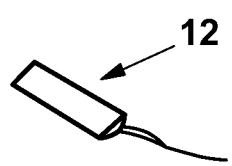
FIG. 7 shows a vibrating motor for the vibrotactile haptic device of FIG. 6, according to an exemplary embodiment.

In particular, vibrating motor 12 can be a Precision Microdrives 303-100 Pico Vibe 3.2 mm motor. Vibrating motor 12, diagrammatically shown in FIG. 7, has preferably a cylindrical shape, and arranged within a cylindrical protection container, not shown, made, for instance, in ABS.

Vibrotactile haptic device 11 can be supplied by Li-Ion batteries, not shown, suitable to assure an autonomy of about 4 hours with the above motor always on.

As an alternative, in an exemplary embodiment, not shown, motor 12 can be a voice coil-type motor, in which the generated vibration amplitude and frequency can be controlled independently from each other.

Figure 8:
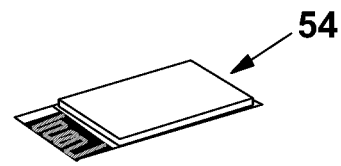
FIG. 8 shows a Bluetooth® module or antenna of the vibrotactile haptic element of FIG. 6.

Actuation unit 14 comprises a receiving module, preferably a Blueetooth module or antenna 54, diagrammatically shown in FIG. 8, for receiving signals 15 obtained from control unit 17 (FIG. 1).

Figure 9:
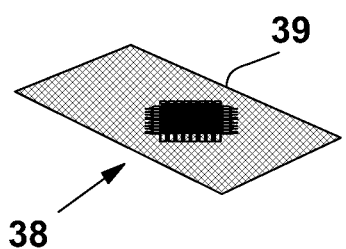
FIG. 9 shows a motor control module of the vibrotactile haptic element of FIG. 6.

Blueetooth antenna or module 54 can be for example a Microchip Technology Inc. RN42 module, which is configured to provide a 3.0/2.0/1.2/1.1 Blueetooth connection. For communication between control unit 17 and vibrotactile haptic device 11 a 9600 baud rate is preferably used. Actuation unit 14 also comprises a control module 12' of vibrating motor 12, shown in FIG. 9 in an embodiment thereof. For instance, control module 38 comprises an Arduino Pro Mini 3.3 V electronic board on which a microcontroller 39 can be installed, such as an ATmega 328 microcontroller.

Preferably, portable telecommunication device 16 is a smartphone, a tablet or an equivalent advanced telephone device, preferably one that is easy to be carried by the subject or the sport or rehabilitation trainer. In this case, wireless transmission means 18 comprises a Blueetooth of the telephone device, with which Blueetooth module 54 of actuation unit 14 is compatible. Similarly, the program means of control unit 17 can comprise an application of the system according to the invention, whereas control unit 17 comprises components of the telephone device in which this application is resident or run.

Figure 11:
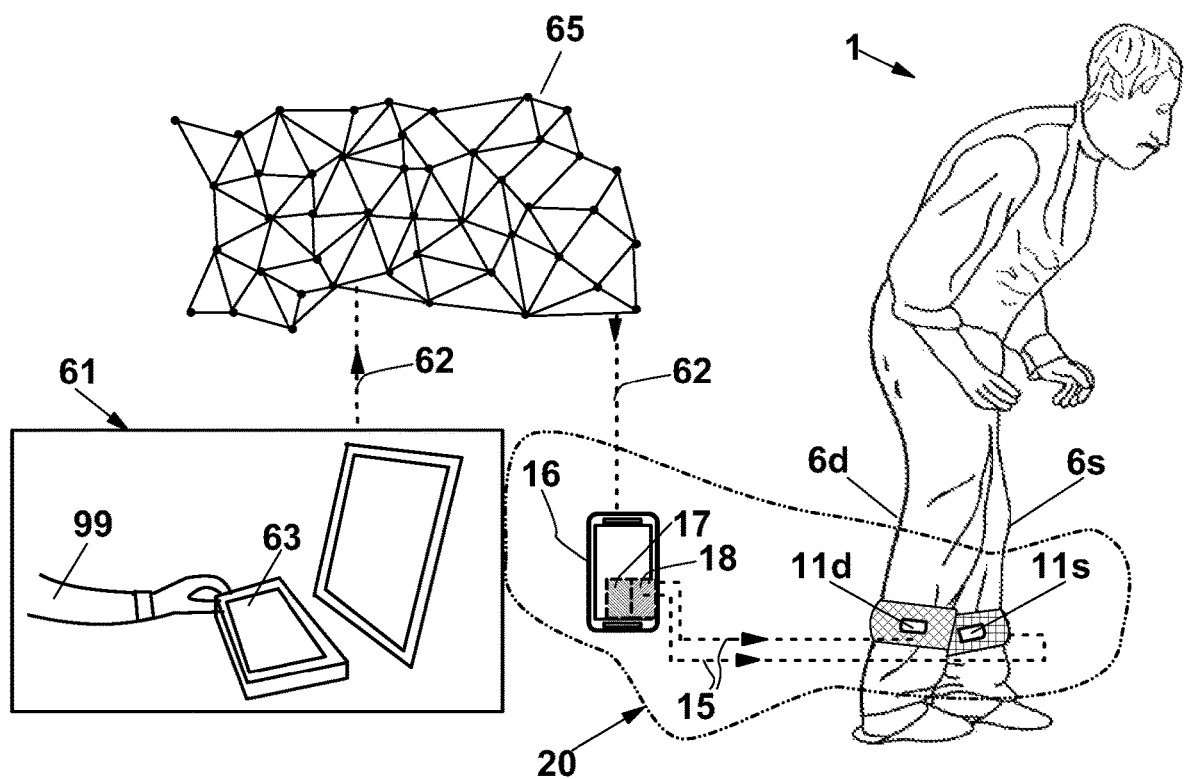
FIG. 11 shows the system of FIG. 10 for a rehabilitation purpose by a remote rehabilitation trainer.

System 20 of FIGS. 10 and 11, according to another exemplary embodiment of the invention, comprises two vibrotactile devices 11d,11s, in this case a right vibrotactile device 11d and a left vibrotactile device 11s, configured to be tightly worn on a right body part 6d and on a left body part 6s of subject 1. In particular, vibrotactile devices 11d,11s are configured to be tightly worn on right leg 6d and the left leg 6s, respectively, of subject 1, to whom a gait cadence must be provided.

In this exemplary embodiment, control unit 17 of telecommunication device 16 is configured to transmit wireless signals 15 to right and left actuation units, not shown, such as actuation unit 14 of vibrotactile device 11 of FIG. 6, so that the latter transfer electrical drive signals alternately to motors 12 of right and left vibrotactile devices 11d,11s, globally respecting the pulse rate generated by the program means, set between 0.5 and 3 per second.

In particular, FIGS. 10 and 11 refer to an use of system 20, or of a modification or exemplary embodiment thereof, according to the invention, for motion rehabilitation of a subject 1 who walks irregularly and/or asymmetrically, for instance, a subject suffering from a nervous system disease such as Parkinson's disease or from peripheral neuropathy. An irregular and asymmetrical gait causes in turn various troubles, in particular joint complications. Medical investigations and tests on a plurality of patients have shown that, by alternately stimulating subject's 1 right leg 6d and subject's 1, a cadenced and symmetrical gait can be restored in subject 1.

The target step rate can be indicated to the patient through a haptic system in which a single vibrotactile device 11 is provided and is arranged on a body part that can also be different from a leg. To this purpose, for instance, haptic system 10 of FIG. 1 can also be used, which comprises a bracelet vibrotactile device. In any case, using two right and left vibrotactile devices 11d,11s, and wearing them on legs 6d,6s assists understanding the gait cadence instructions, in particular, for a subject with reduced cognitive function.

In a first modification, or in a first mode of use, as shown in FIG. 10, system 20 can be used autonomously. In this case, the cadence signals generation program that is resident in control unit 17 of telecommunication device 16 comprises values of cadence pulse rate and duration of exercise duration to be carried out by subject 1, and is started by subject 1 itself or by a trainer.

In a second modification, or in a second mode of use, as shown in FIG. 11, system 20 can be used under a remote assistant's 99 supervision. In this case, system 20 is configured to be connected to, or comprises, a remote control unit 61, which can comprise a personal computer or an equivalent device. Remote control unit 61 has a CPU, and is configured to receive an assistance request sent through telecommunication device 16 and to interface with a remote operator 99. Remote control unit 61 comprises a remote input means 63 through which remote operator 99 can set and modify the operation parameters of system 20, generating instructions 62. Control unit 17 is configured to receive instructions 62 from a data network 65, such as internet, and for transforming them into cadence signals 17' (figure) and then into wireless signals 15, through wireless transmission means 18.

Figure 12:
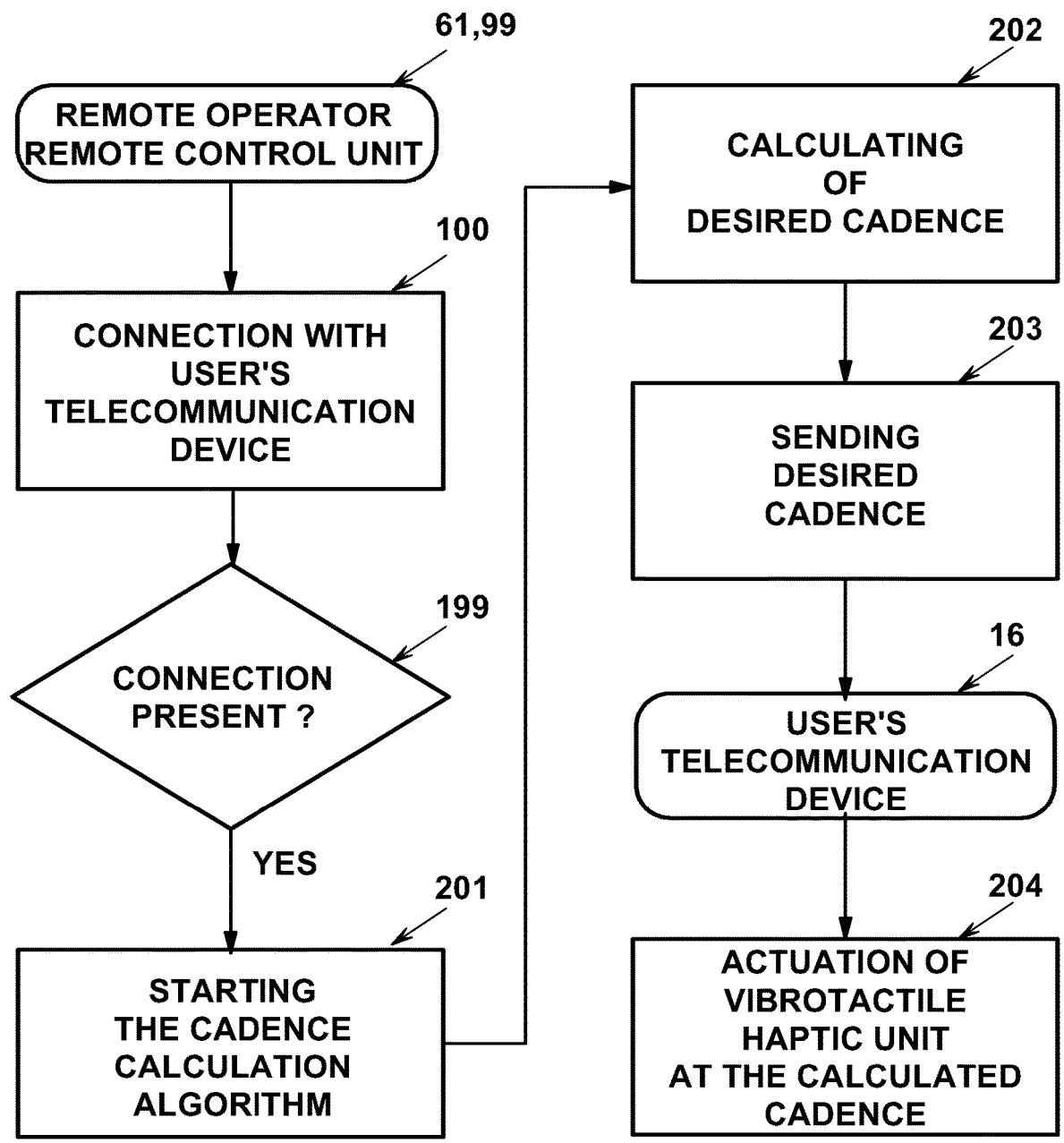
FIG. 12 is a block diagram describing the operation of a system according to the exemplary embodiments shown in FIGS. 1, 10, 11.

The operation of system 20 is now described with reference to FIGS. 11 and 12, in the second modification or mode of use. Remote operator 99, after a step of assessing mutual availability with subject 1, performs a step 100 of connection with telecommunication device 16 of subject 1, or of an assistant of the latter, through remote control unit 61. This can occur, for instance following a subject's 1 request.

Once a step 199 of checking the presence of a connection, remote control unit 61 starts and performs a step 210,202 of calculating a predetermined cadence, according to some parameters of subject 1, which are known by the remote operator or are recorded in remote control unit 61. Then, the remote control unit associates the calculated cadence to an instruction packet 62 and carries out a step 203 of sending instructions 62 to portable telecommunication device 16, through data network 65, using a conventional communication protocol. Upon receiving instructions packet 62, the program, which is resident in control unit 17 of telecommunication device 16, carries out a step 204 of alternately actuating vibrotactile haptic units 11d,11s at the calculated cadence during a predetermined time, which is locally set in telecommunication device 16 or is received along with instruction packets 62.

Figure 13:
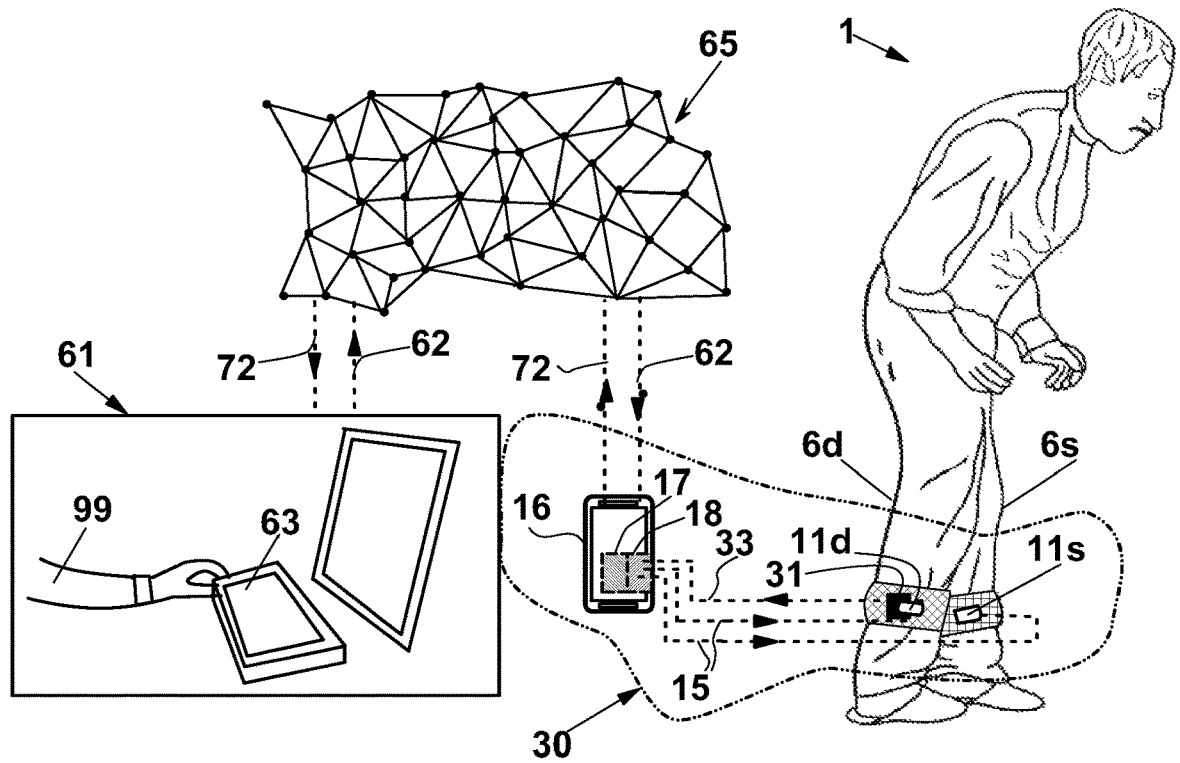
FIG. 13 shows a system according to a modification of the system of FIGS. 10 or 11, in which a sensor is provided, in this case an accelerometer, configured to provide a position signal of a lower limb of the subject, for a rehabilitation purpose by a remote rehabilitation trainer.

FIG. 13 shows a haptic system 30 according to a further exemplary embodiment, which differs from device 20 in that it comprises a sensor 31 configured to provide position signals 33 of subject's 1 lower limb 6d, preferably as position wireless signals 33. In this case, the sensor is an accelerometer 33.

As well known, in a normal deambulation activity, i.e. in a subject's walking or running activity, during each step or jump, respectively, each point of the subject's body cyclically modifies its speed, and so cyclically modifies its acceleration as well. This cyclical variation is remarkable for each point of the subject's legs. The time interval between two corresponding points of two consecutive acceleration cycles, or of a component thereof, for example the time interval between two points where acceleration is at a maximum, represents therefore the gait cadence of the subject's walking or running activity. Therefore, by extracting the maximum values from the acceleration measured values, and by measuring the time interval between two consecutive maximum points, i.e. the number of maximum points that occur in a given time unit, a true gait cadence value is obtained pertaining the subject's running or walking activity.

Such step of extracting the acceleration maximum values and of calculating the true gait cadence can be carried out directly by an advanced accelerometer 31, or by control unit 17, to which accelerometer 31 provides all the measured acceleration data. In other words, accelerometer data 33 can be already cadence data, or raw accelerometer data.

In the light of the above, accelerometer 31 is preferably integral to one of vibrotactile devices 11d,11s of device 30, in particular if these are worn on the subject's legs. In this exemplary embodiment, actuation unit 14 (FIG. 6) is configured to provide portable telecommunication device 16 with wireless accelerometer signals 33, which are received and recorded in a memory unit, not shown.

However, the sensor can be also a different type sensor, for instance it can be a contact or pressure sensor arranged between lower limb 6d the soil, for example it can be integrated in the insole or in the heel of a shoe worn by subject 1 to be rehabilitated Moreover, control unit 17 of system 30 is configured to receive such position signals 33 of limb 6d, and the program resident in it is configured to form a limb 6d position data packet 72, and to send it to remote control unit 61. This way, remote assistant 99 can receive a feedback of subject's 1 performance and, according to this feedback, can modify the rate of cadence pulse 19 (FIG. 1).

In a modification of system 30 of FIG. 13, control unit 17 is configured to modify the rate of cadence pulse 19 responsive to wireless accelerometer signals 33.

Figure 19:
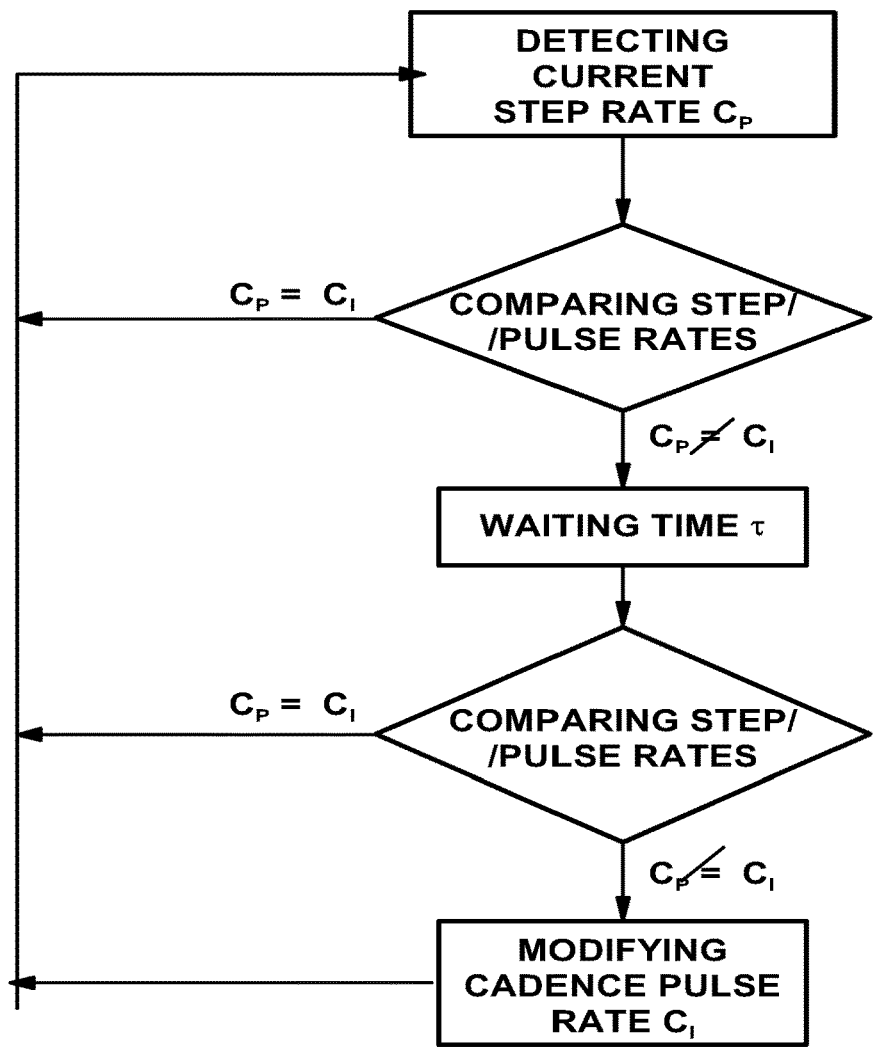
FIG. 19 is a flow diagram of a procedure of adjusting the cadence pulse rate provided by a system according to the invention to a subject's current step rate.

In a further modification, control unit 17 is configured to operate as shown in the flow-sheet of FIG. 19, i.e. to determine the current step rate according to wireless accelerometer signals 33, in order to compare it with an actual cadence pulse rate, and for changing the actual cadence pulse rate so as to obtain a modified cadence pulse rate corresponding to the current step rate, if the current step rate is not modified after a predetermined time, in particular, set between 5 and 10 seconds.

Figure 14:
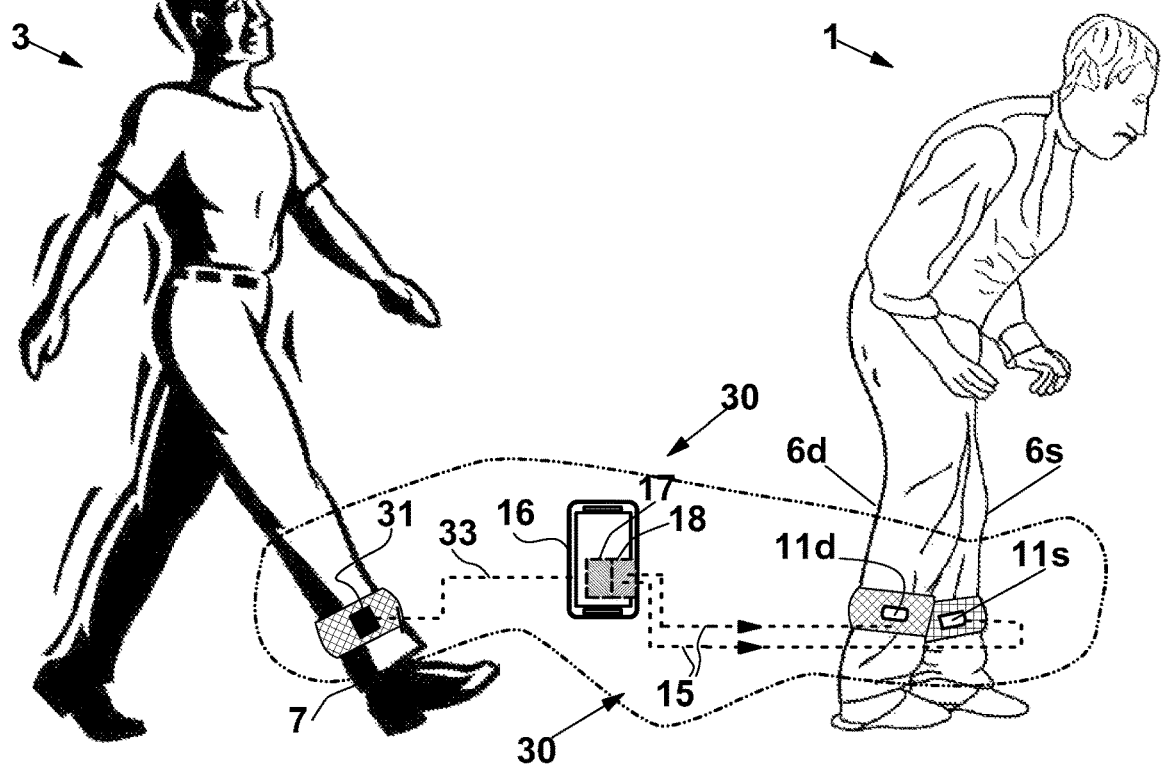
FIG. 14 shows the system of FIG. 13, for a rehabilitation purpose by a local rehabilitation trainer.

FIG. 14 shows a different operation mode of system 30, where sensor 31 is arranged integral to a lower limb 7 of a local rehabilitation trainer or assistant 3 who makes subject 1 tio perform a motion rehabilitation procedure. In this case, sensor 31 can provide position signals 33 of leg 7. Control unit 17 is configured to receive signals 33, and the cadence pulse generation program, which is resident therein, is configured to modify the rate of cadence pulse 19 (FIG. 6) responsive to the position signals. This way, subject 1 to be rehabilitated perceives rehabilitation trainer's 3 step rate through vibrations 13. In other words, rehabilitation trainer 3, walking at a given step rate, decides which step rate must be required to subject 1.

Figure 15:
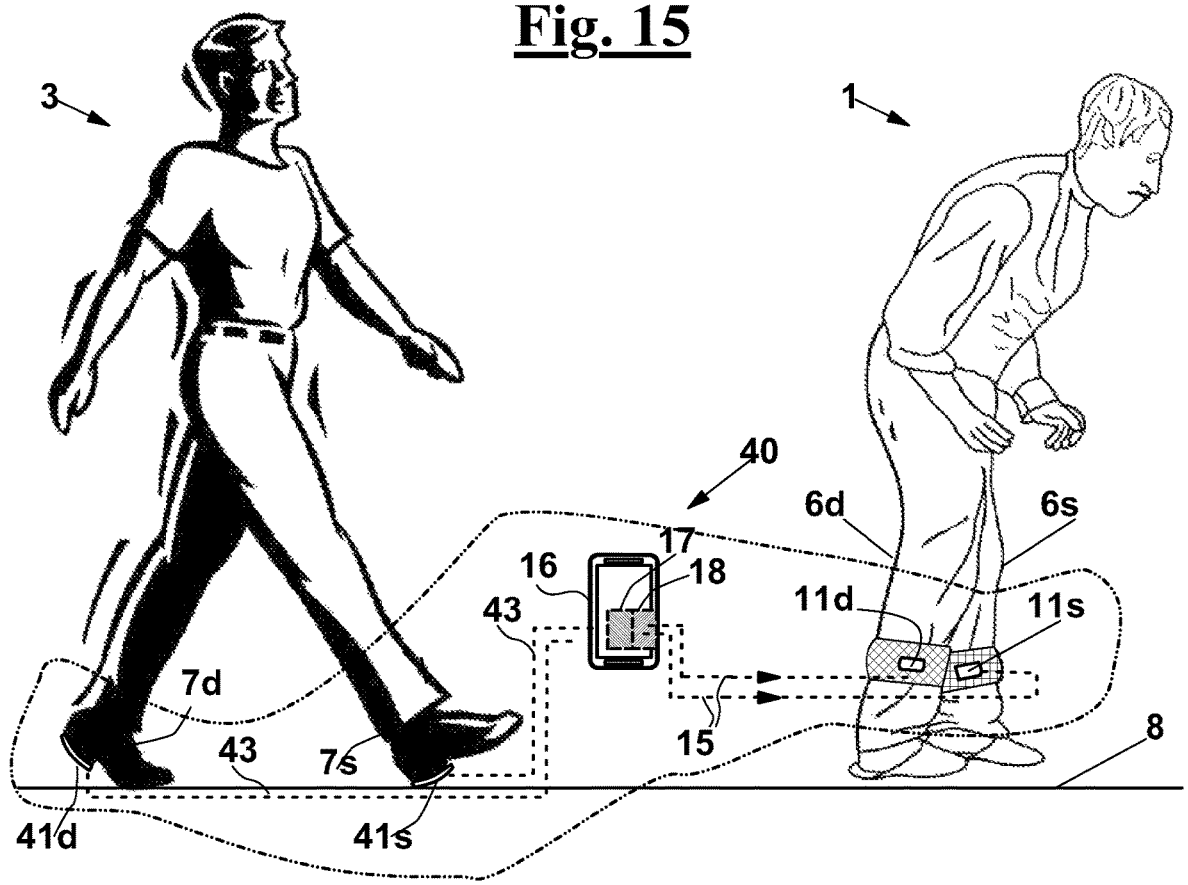
FIG. 15 shows a system according to a modification of the system of FIG. 12, in which a couple of sensors is provided for measuring the position of both lower limbs, and wherein said sensor is a sensor of contact or of pressure.

FIG. 15 shows a system 40, according to an exemplary embodiment of the invention, which is used as described with reference to FIG. 14. System 40 differs from system 30 in that it comprises, instead of accelerometer 31, two right and left pressure sensors 41d,41s stably arranged between right and left foot 7d,7s, respectively, and soil 8, and also differs therefrom in that control unit 17 is configured to receive position signals 43 of rehabilitation trainer's 3 two lower limbs 7d,7s. The program resident in control unit 17 is configured to analyse signals 43 as described for signal 33 with reference to FIG. 14.

By such an arrangement of pressure sensors 41d,41s of FIG. 15, signals 43 contain pulses that correspond to steps in which rehabilitation trainer's 3 heels are in contact with soil 8, but the sensor can be positioned otherwise, in order to detect the contact with soil 8 of different or wider regions of the soles of feet 7d,7s.

With reference to FIG. 16, a haptic system 50 is described according to a further exemplary embodiment, comprising a first couple of right and left vibrotactile devices 11d,11s and a second couple of right and left vibrotactile devices 21d, 21s, each couple to be used by a first subject 1 and a second subject 2, respectively. For subjects 1,2 the system comprises first and second portable telecommunication devices 16,26, respectively, comprising respective control units 17,27 and respective wireless transmission means 18,28 for transmitting wireless signals 15 to first couple 11d,11s and to second couple 21d,21s, respectively, of vibrotactile devices, more precisely to respective actuation units 14,24, so that the latter generate and send corresponding cadence pulses 19,29 to motors 12,22, and these produce respective vibrations 13,23 that can be perceived by subjects 1 and 2.

Moreover, system 50 comprises an accelerometer 31, which can be integrally mounted to one of vibrotactile devices 11d,11s of one of the two couples, in this case the first couple. Corresponding control unit 17 is configured to measure a first current step rate of subject 1 starting from wireless accelerometer signals 33 obtained from accelerometer 31, and for communicating this first current step rate, through data network 65, to second portable telecommunication device 26, with which second subject 2 is provided, in the form of data packets 82. Control unit 27 of the second portable transmission device is configured to extract the position signals associated to accelerometer signals 33 from packets 82, and the generation program resident therein is configured to modify the rate of cadence pulse 29, sent to right and left actuation units 24, responsive to said position signals, in particular it is configured to generate cadence pulses 29 with the same rate as the current step rate of first subject 1, so that motors 22 transfer corresponding vibrations 23 to lower limbs 6d,6s of second subject 2, this way proposing the current step rate of first subject 1, which plays the role of the main subject, to second subject 2, who plays the role of a subordinate subject.

FIG. 17 shows a system 50', according to another exemplary embodiment of the invention, which differs from system 50 in that it provides a single vibrotactile device 11,21 for each subject 1,2. In particular, vibrotactile device 11, with which the first subject is provided, is similar to device 11 of FIG. 16, or is similarly positioned on the right leg of subject 1, whereas vibrotactile device 21, with which the second subject is provided, is configured to be tightly worn about waist 6 of subject 2.

Subjects 1 and 2 of FIGS. 16 and 17 are typically two subjects who are far away from each other. The system according to the invention enables these subjects 1 and 2 to walk or run synchronizing their own gait cadence, which is an activity indicated here as "social running".

Figure 18:
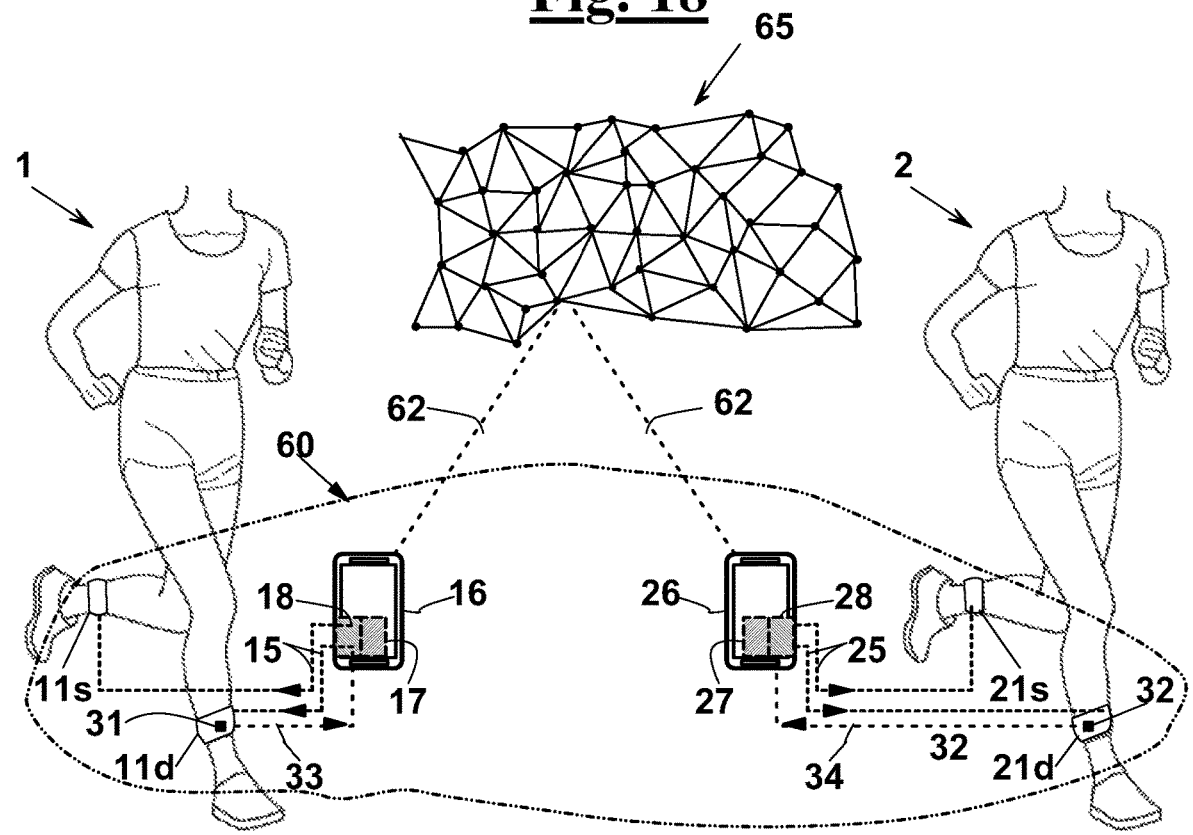
FIG. 18 shows a system according to a modification of the exemplary embodiment shown in FIG. 17, in which sensors are provided for measuring the position of the lower limbs of both the subjects performing a social running session.

FIG. 18 shows a haptic system 60, according to a modification of system 50 of FIG. 16, comprising two accelerometers 31 and 32, with which the first subject and the second subject 1,2 are provided. This way, subjects 1 and 2 can swap their roles of main subject and subordinate subject. To this purpose, second control unit 27 is configured to measure a second current step rate related to the steps of second subject 2, starting from wireless accelerometer signals 34 obtained from accelerometer 32, and is also configured to communicate this second rate to first portable telecommunication device 16, with which the first subject is provided, in the form of data packets 92. Control unit 17 of first portable transmission device 16 is configured to extract the position signals associated to accelerometer signals 34 from packets 92 and the generation program resident therein is configured to modify the rate of cadence pulse 19, sent to right and left actuation units 14, responsive to said position signals, in particular it is configured to generate cadence pulses 19 with the same rate as the current step rate of second subject 2, so that motors 12 transfer to lower limbs 6*d*,6*s* of first subject 1 corresponding vibrations 13, this way proposing the current step rate of second subject 2 to first subject 1, who in this case can play the role of a subordinate subject.

Figure 20:
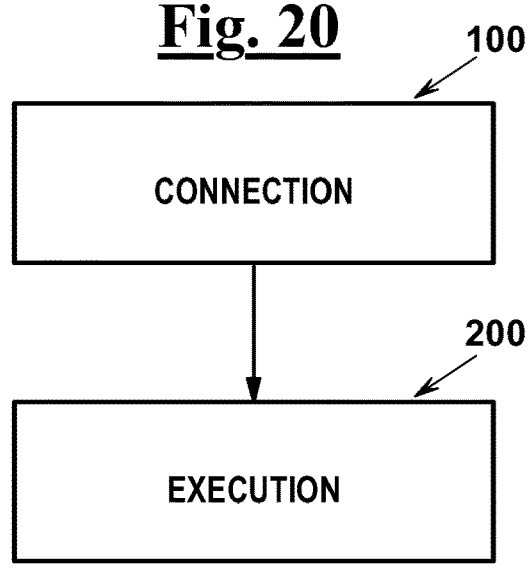
FIGS. 20-22 are flow diagrams describing the operation of the system of FIG. 17 and an operation mode of the system of FIG. 18.
Figure 21:
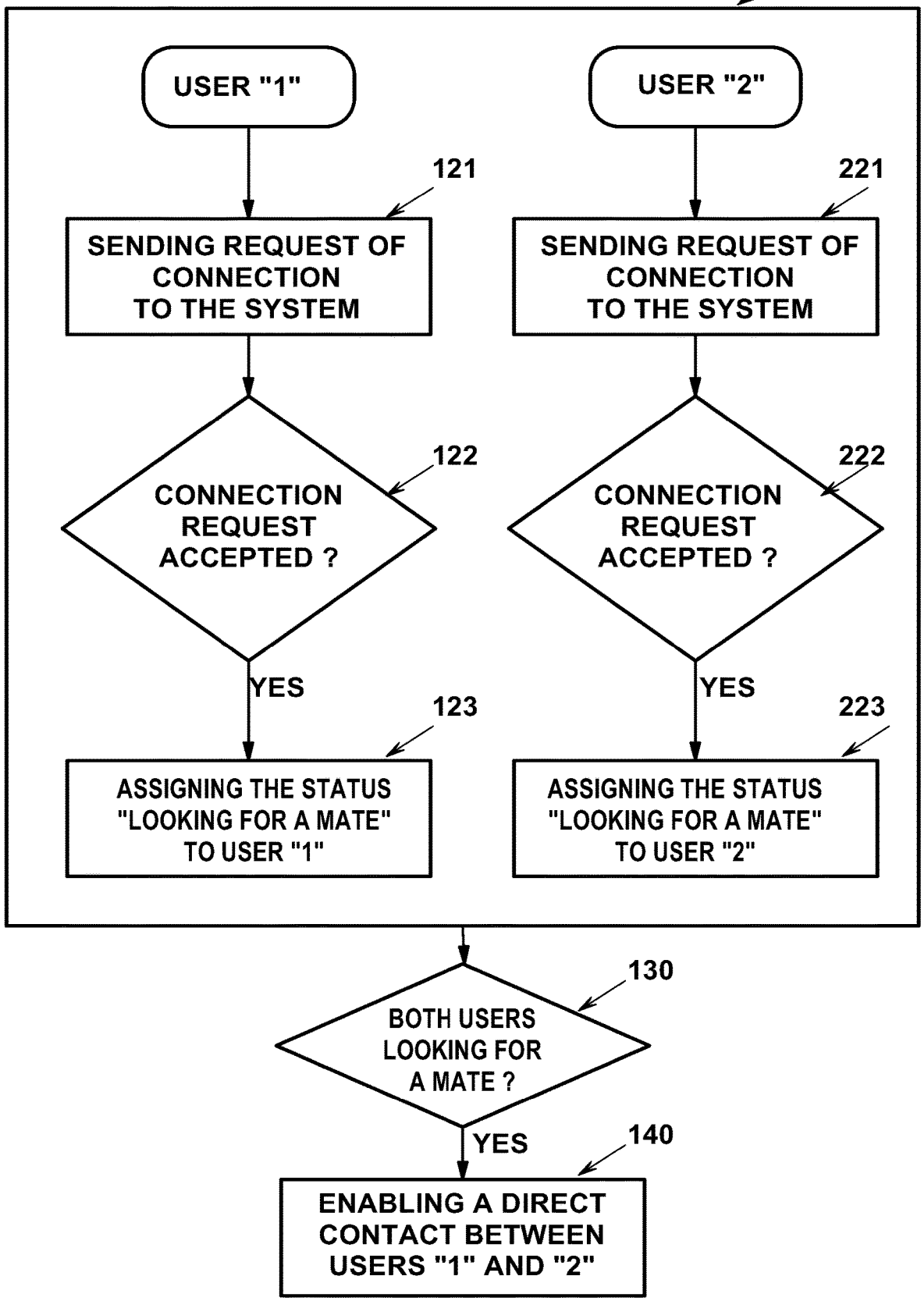
Figure 22:
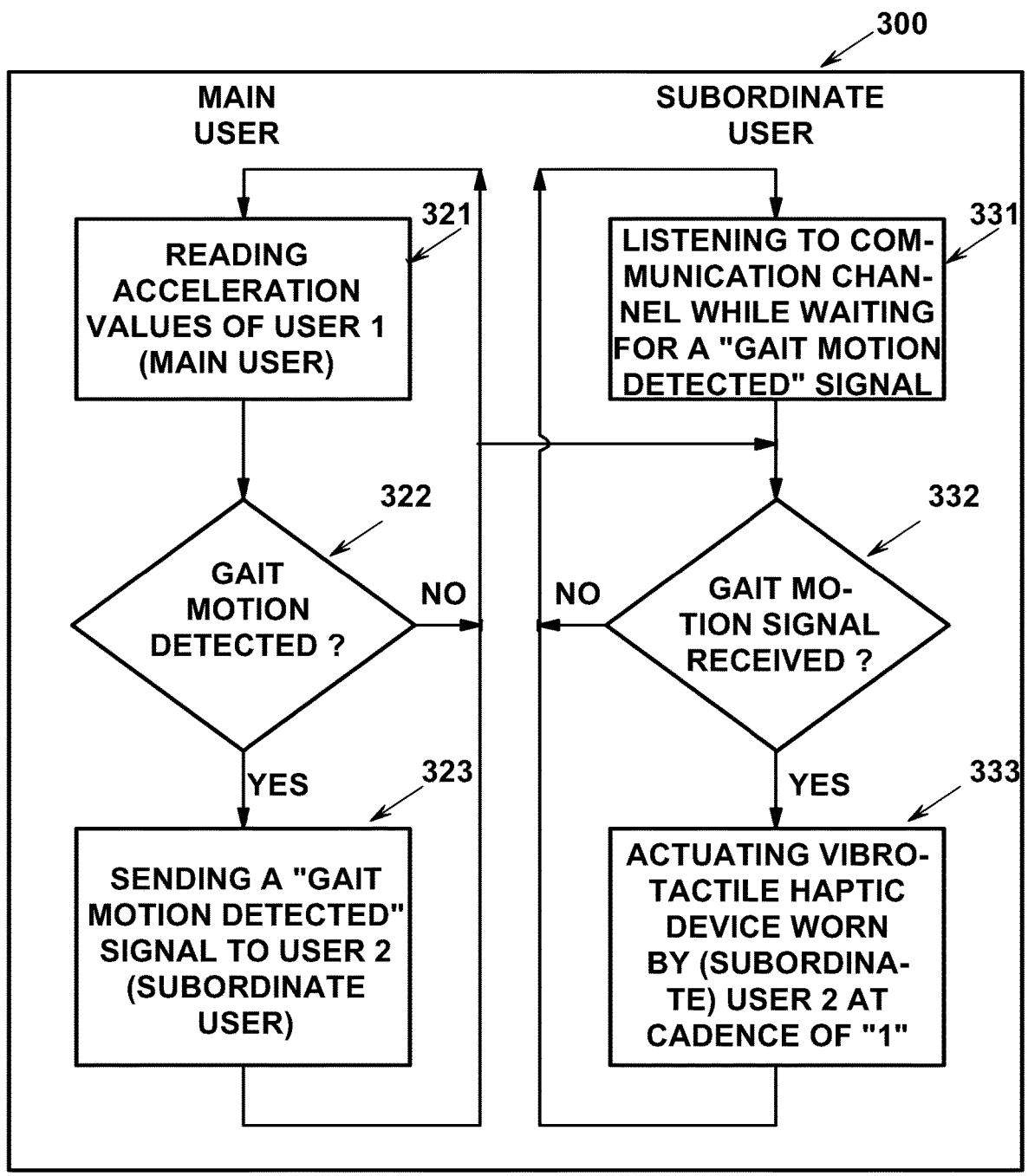

With reference to FIGS. 20-22, the operation of system 50 is now described, which comprises (FIG. 20) a step 100 of connecting subjects 1 and 2, i.e. of connecting respective telecommunication devices 16,26, and a step 300 of performing a "social running" activity by two subjects 1 and 2.

In connection step 100, shown by the block diagram of FIG. 21, it is assumed that at least at two subject or users 1 and 2, who are in any case far away from one another, are both interested in a social running activity. Users 1 and 2 can choose among activities that can differ from each other by some features of the path available for running, such as altimetry data, speed general parameters to be respected, general difficulty rate, which define different activity classes. Users 1 and 2 connect themselves to a server, not shown, through a portal that controls the social running service, which is available through respective telecommunication devices 16,26, and perform respective steps 121, 221 of requesting a connection to system 50, or 60, described below. The remote server performs steps 122,222 of evaluating the two requests and, if they are accepted, it also performs steps 123,223 of assigning the status of "user looking for a mate" to users 1 and 2, who are typically identified by their own server connection credentials.

The above assignment normally occurs at different times for the two or more subjects, whereby the server periodically performs a step 130 of checking the presence of couples or even of plurality of users who are interested in social running activities of the same class or, in any case, who are compatible with one another in connection with the difficulty and other issues. If a couple is present of users 1 and 2 who are interested in a same class and who have received status of "user looking for a mate", the server carries out a step 140 of enabling these users to get in contact with each other. In this case, a menu for choosing a possible mate can be displayed on the communication device of each user 1,2. Upon mutual acceptance of a contact between two or more users 1,2, a communication channel is activated between portable telecommunication devices 16 and 26, through which data packets 82, 92 (FIGS. 17,18) are transferred.

Once this contact has been established, the social running comes into execution step 300, illustrated by the block diagram of FIG. 22, which considers users 1 and 2 engaged in a running or in a walking activity. User 1, as indicated in FIGS. 17 and 18, has an accelerometer 31, while user 2 may not have (FIG. 17) or may have (FIG. 18) of an own accelerometer 32.

Control unit 17 of telecommunication device 16 of first user 1 cyclically performs steps 321 of reading the acceleration of first subject 1 and 322 of detecting a gait motion. In other words, control unit 17 checks if accelerometer signals 33 obtained from accelerometer 31 can be related to a gait motion, according to predefined parameter values. As an alternative, as anticipated when describing FIG. 13, the accelerometer signals can be previously filtered by accelerometer 31, in which case they only contain the contributes of steps or jumps, which normally correspond to the maximum value of an acceleration component that changes cyclically.

If accelerometer signals are present that can be related to a step or to an elementary running act, i.e. a jump, control unit 17 causes telecommunication device 16 to perform a step 323 of sending a "gait motion detected" signal to telecommunication device 26 of second user 2, which contains the acceleration or step rate values of user 1, through data network 65 (FIGS. 17 and 18). Control unit 27 of telecommunication device 26 permanently carries out a step 331 of listening to the communication channel activated upon establishing the contact. Upon detecting the "detected gait motion" signal sent by control unit 17, and the corresponding acceleration value, step 332, control unit 27 carries out a step 333 of actuating of vibrotactile haptic devices 21*d*,21*s* (FIGS. 16 and 18), or a single vibrotactile haptic device, in a modification of system 50 or 60, so that corresponding actuation unit 14 transfer cadence pulses 19 to motor 12 (FIG. 6), according to the rate of accelerometer signal 33, this way suggesting user 2 to synchronize his/her own steps or elementary running acts, to this rate.

The diagram of FIG. 22 relates to the case where user 1 plays the role of main user, who decides the cadence to be followed by the other user or users by his/her own gait, whereas user 2 plays the role of subordinate user. This configuration is enabled by the system as in FIGS. 16 and 17. FIG. 18, due to second accelerometer 32, with which second user 2 is provided, makes it possible to exchange roles between user 1 and user 2, with obvious modifications of the diagram of FIG. 22. FIG. 23 is a diagram for the latter case, which summarizes the elements of system 60 and the steps of the procedure carried out by system 60. These elements, not identified with words, can be recognized by reference numbers.

Figure 25:
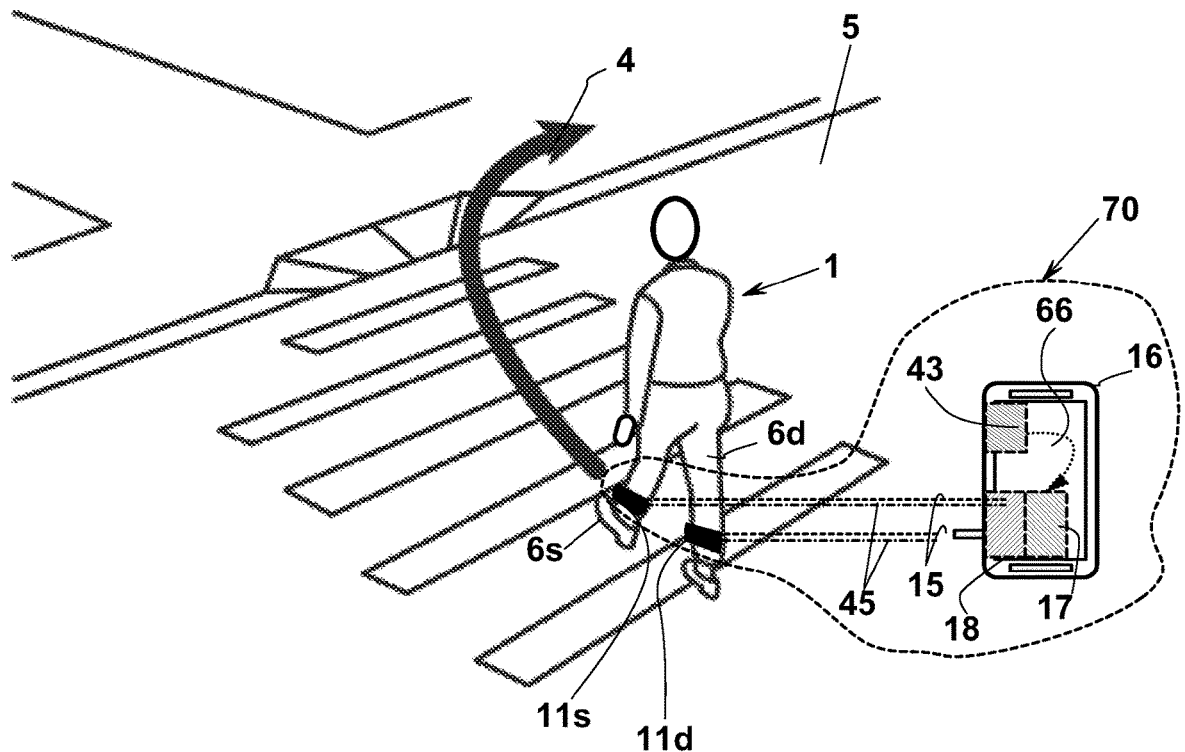

The systems according to the above-described exemplary embodiments (FIGS. 1,10,13,17,18) may have respective modifications 70 or 80, as diagrammatically shown in FIGS. 24 and 25. In these modifications, portable telecommunication device 16 comprises a navigation system 43 configured to generate direction signals 66 responsive to a predetermined path 4 selected by subject 1 by him/herself, or for subject 1 by an assistant. Control unit 17 of telecommunication device 16 is configured to transmit further wireless signals 45 to the actuation unit or units 14 (FIG. 25) of vibrotactile devices 11d,11s, responsive to direction signals 66, besides signals 15 of FIG. 1, so that actuation unit 14 transfers direction pulses 49 to a further motor 42, in which direction pulses 49 have at least one feature different from cadence pulses 19 that actuate motor 12. This feature can be selected, for instance, between the rate and the intensity of cadence pulses 19.

For example, subject 1 of FIG. 25, who follows path 4, will receive a turn right indication once he has crossed the street 5, preferably, in the form of vibrations generated by the right vibrotactile device 11d worn on right leg 2d, through further motor 42.

Figure 26:
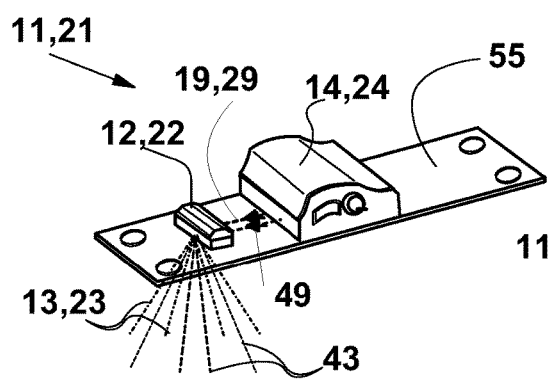
FIG. 26 diagrammatically shows the operation of the vibrotactile device of FIG. 6, having one motor only, in the system of FIG. 26 or of FIG. 27.

In a modification, shown in FIG. 26, vibrotactile devices 11d,11s comprise a single motor 12 as in FIG. 6, configured to generate cadence pulses 19 and 49 that can be distinguished by subject 1 by at least one feature different from one another, selected, for instance, as indicated above, and is configured to transfer these cadence and direction pulses 19,49 to single motor 12.

Figure 27:
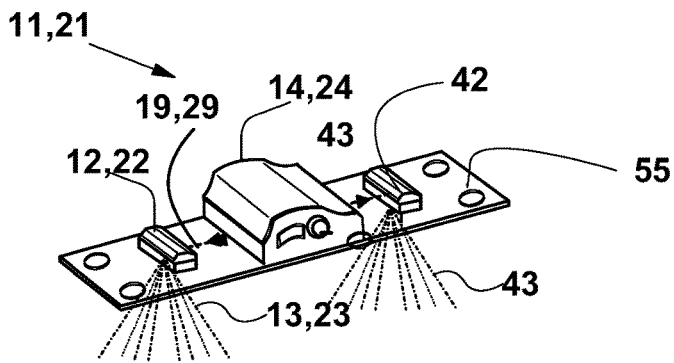
FIG. 27 diagrammatically shows a vibrotactile haptic device comprising two motors to generate gait pulses and direction pulses for the system of FIG. 26 or of FIG. 27, respectively.

FIG. 27 shows a vibrotactile device 11d,11s, suitable for haptic systems 70 and 80. This vibrotactile device differs from the device of FIG. 6 in that it comprises, besides motor 12, further motor 42, which is also configured to generate vibrations. Actuation unit 14 is configured to receive, besides wireless signals 15, further wireless signals 45 that control unit 17 causes to be emitted by wireless transmission means 18 according to direction signals 66, and is also configured to transfer direction pulses 49 to motor 42 responsive to wireless signals 45.

The foregoing description of exemplary embodiments of the invention will so fully reveal the invention according to the conceptual point of view, so that others, using the prior art, will be able to modify and/or adapt in various applications the specific exemplary embodiments without further research and without parting from the invention, and, accordingly, it is meant that such adaptations and modifications will have to be considered as equivalent to the specific embodiments. The means and the materials to carry out the different functions described herein could have a different nature without, for this reason, departing from the field of the invention. It is to be understood that the phraseology or terminology that is employed herein is for the purpose of description and not of limitation.

The invention claimed is:

1. A haptic system for providing a gait cadence to a subject, said haptic system comprising:
a portable telecommunication device comprising a control unit and a wireless transmission means;
a vibrotactile device configured to be tightly worn on a portion of said subject's body, and comprising:
a motor configured to generate vibrations that are able to be perceived by said subject;
an actuation unit configured to actuate said motor,
wherein said actuation unit is configured to receive wireless signals from said wireless transmission means of said portable telecommunication device and to cause said motor to produce vibrations responsive to said wireless signals;
in said control unit a generation program is resident configured to generate cadence signals and to transmit said wireless signals responsive to said cadence signals by said wireless transmission means of said portable telecommunication device to said actuation unit;
said generation program configured to provide corresponding cadence pulses to said motor, in order to cause said motor to generate said vibrations in such a way that said subject is able to cadence the gait responsive to said cadence pulses, said generation program configured to generate, through said cadence signals:
a cadence pulse rate set between 0.5 and 3 pulses per second;
a single pulse duration set between 0.1 and 1.0 second;
a repetition of said pulses for at least 30 seconds; and
a sensor configured to provide to said control unit position signals of when a foot of a lower limb in a gait cycle is in contact with a ground;
wherein said sensor is selected from the group consisting of:
a pressure or contact sensor, and said position signals are pressure or contact signals of a foot of said lower limb with the ground; and
an accelerometer, and said position signals are accelerometer signals configured to indicate when a foot of said lower limb is in contact with the ground;
wherein said generation program, which is resident in said control unit, is configured to modify said cadence pulse rate responsive to said position signals.

2. The haptic system according to claim 1,
wherein said vibrotactile device is a right vibrotactile device;
wherein said motor is a right motor; and
wherein said actuation unit is a right actuation unit;
wherein the haptic system further comprises:
a left vibrotactile device;
a left motor; and
a left actuation unit;
wherein said right and left motors are configured to generate vibrations that are able to be perceived by said subject;
wherein said right and left actuation units are configured to actuate said right motor and said left motor, respectively, and
wherein said right and left actuation units are configured to be tightly worn on a right part and on a left part of said subject's body, respectively, and wherein said generation program is configured to cause said right motor to generate right cadence pulses, and said left motor to generate left cadence pulses, said right and left cadence pulses being provided alternately, a sum of said right and left cadence pulses corresponding to said cadence pulse rate.

3. The haptic system according to claim 1, wherein said sensor is separate from said vibrotactile device.

4. The haptic system according to claim 1, wherein said sensor is integral to said vibrotactile device.

5. The haptic system according to claim 1, wherein said control unit is configured to:
measure a current step rate according to said position signals;
comparing said current step rate with a current value of said cadence pulse rate;
and wherein said generation program, which is resident in said control unit, is configured to modify said cadence pulse rate from said current value to a modified value corresponding to said current step rate, if said current step rate is not modified within a predetermined time set between 5 seconds and 10 seconds.

6. The haptic system according to claim 1, wherein said subject is a first subject;

said portable telecommunication device is a first portable telecommunication device with a first control unit and a first wireless transmission means, said vibrotactile device is a first vibrotactile device with a first motor and a first actuation unit, wherein said haptic system further comprises:

a second portable telecommunication device comprising a second control unit and a second wireless transmission means;

a second vibrotactile device comprising a second motor configured to generate vibrations that are able to be perceived by a second subject and comprising a second actuation unit configured to actuate said second motor;

said generation program resident in said first control unit is a first generation program;

wherein said first control unit is configured to measure a first current step rate starting from said position signals provided by said sensor, and for wirelessly communicating said first current step rate to said second portable telecommunication device, wherein, in said second control unit, a second generation program is resident configured to generate cadence signals and to transmit said cadence signals through said second wireless transmission means to said second actuation unit, wherein said second actuation unit is configured to receive wireless signals from said second wireless transmission means and to cause vibrations of said second motor responsive to said wireless signals, so that the first subject who wears said first vibrotactile device is able to haptically communicate his/her own cadence to the second subject who wears said second vibrotactile device.

7. The haptic system according to claim 6, wherein a second sensor is provided integral to said second vibrotactile device configured to provide position signals of said second subject's lower limb in a gait cycle, wherein said second control unit is configured to measure a second current step rate of said second subject starting from position signals coming from said second sensor, and for communicating said second current step rate to said first portable telecommunication device, such that said first subject and said second subject are able to haptically synchronize their own gait cadences with each other.

8. The haptic system according to claim 7, wherein said first and second generation programs, which are resident in said first and second control units, respectively, are configured to cause said right motor and said left motor, respectively, to generate corresponding cadence pulses having a cadence equal to an average value of cadences detected starting from said position signals.

9. A haptic system according to claim 1, wherein said motor is selected from the group comprised of:

a motor comprising a driven rotating shaft including an eccentrical portion;

a voice coil-type motor.

* * * * *